United States Patent [19]

Kadkade

[11] 4,060,933
[45] Dec. 6, 1977

[54] TISSUE CULTURE TECHNIQUE UTILIZING A SPECIFIC LIGHT SOURCE

[75] Inventor: Prakash G. Kadkade, Marlborough, Mass.

[73] Assignee: GTE Laboratories Incorporated, Waltham, Mass.

[21] Appl. No.: 752,485

[22] Filed: Dec. 20, 1976

[51] Int. Cl.$^2$ ............................................. A01G 1/00
[52] U.S. Cl. .................................... 47/58; 47/DIG. 6
[58] Field of Search ............................. 47/58, DIG. 6

[56] References Cited

U.S. PATENT DOCUMENTS

| | | | |
|---|---|---|---|
| 3,514,900 | 6/1970 | McDade | 47/58 |
| 3,683,550 | 8/1972 | Corlett et al. | 47/58 |
| 3,816,960 | 6/1974 | Gudin et al. | 47/58 |

FOREIGN PATENT DOCUMENTS 1,387,821  3/1975  United Kingdom .................... 47/58

*Primary Examiner*—Robert E. Bagwill
*Attorney, Agent, or Firm*—Irving M. Kriegsman; Robert A. Seldon

[57] ABSTRACT

One aspect of the invention comprises a method for stimulating organogenesis of explants in a tissue culture comprising the step of illuminating the explant culture during at least a portion of its differentiation stage with light having a predominate spectral emission of approximately 660nm.

A second aspect of the invention includes the additional illumination of the explants with 740nm light, subsequent to an intervening period of preferably one to two weeks. The 660nm light primarily stimulates shoot formation while the 740nm light primarily stimulates root formation. The intervening period precludes photoreversibility of the initially obtained light effects.

11 Claims, 2 Drawing Figures

TISSUE CULTURE TECHNIQUE UTILIZING A SPECIFIC LIGHT SOURCE

FIELD OF THE INVENTION

This invention relates generally to a tissue culture method for the asexual propagation of plants and, more specifically, to the use of a narrow-band light source for promoting organogenesis by the tissue culture.

The conventional propagation of plants through seeds has always suffered a number of limitations. The plants thus propagated may be quite variable, since they do not necessarily contain all the parental characteristics, and a significant proportion of a crop may consequently be of an unsellable quality. Additionally, proper germination of the seeds is dependent upon, and influenced by, such external conditions such as whether, the nature and pH of the soil, organisms in the soil, the availability of water, temperature, light and a loss of vigor during storage of the seeds. The number of seed-propagated plants available for consumption is limited both the seasonal availability of the crop, seed supply and the amount of growing space.

Recent forecasts predicting an increasing food shortage in the world, have stimulated efforts to discover more efficient and reliable methods for food production. In recent years, plant tissue culture methods have gained importance as a means for vegetative propagation of food, ornamental and medicinal crops owing to its ability to produce rapid multiplication and proliferation of genetically uniform plants, thereby assuring that the desired characteristics of the selected donor plants are retained.

In the tissue culture technique, a piece of a donor plant is excised and placed in a culture medium comprising nutrients in the form of organic and inorganic compounds and hormones. Because the size of excised plant parts are generally in the order of 2 or 3 millimeters, the number of cultures which may be induced from a single donor plant, may greatly exceed the number of seeds such a plant would ordinarily produce. The rate of multiplication, thus, obtainable is even further enhanced by the fact that one need not wait for the plants to produce seeds, but may excise plant parts at virtually any time during the plants growth. Accordingly, the tissue culture technique enables timely increases of plant stock and hastens the availability of new varieties. Finally, the minimal size of the excised plant part lends itself to convenient storage under sterile conditions so that pest and plant disease (problems conventionally associated with the maintenance of stock plants) is virtually eliminated.

Conventionally, tissue culture techniques have been tailored to the stages of growth for the particular plant involved. These growth stages may be described as: the induction stage, where the explant is established aseptically on the medium and allow to respond to the medium via a rapid growth and enlargement; the multiplication stage, wherein the explant produces a massive, undifferentiated cells containing callus; the differentiation stage wherein the cells give rise to shoots and/or roots to form a plurality of plantlets; and the hardening stage wherein the plantlets are separated and allowed to develop from the heterotropic to the autotropic stage. During the induction stage, the explants have conventionally been placed in a nutritive medium containing organic and inorganic salts and growth regulators or growth hormones.

An example of a tissue culture technique particularly suited for the hereindescribed invention forms the subject matter of my co-pending U.S. Pat. application Ser. No. 727,323, filed Sept. 27, 1976, assigned to the assignee of the present invention, and hereby incorporated by reference. That application is directed to a tissue culture technique and a culture medium used therewith for asexually propagating a plurality of plants of the family Cruciferae wherein an excised portion of a donor plant is placed in a culture medium comprising organic and inorganic salts and a preferable concentration of 1 mg/1 of indoleacetic acid, 0.5 mg/1 kinetin and 40 mg/1 of adenine sulfate. The medium induces the simultaneous initiation of buds and roots by the explant to form a plurality of plantlets which may be transplanted into soil for the timely initiation of food and medicinal crops. As disclosed in that application, a period of approximately 14 to 30 days is required to generate a plurality of plantlets in the culture medium. For obvious reasons, it is desirable to generate a maximum number of such plantlets. Accordingly, the formation of a maximum number of shoots and roots during differentiation is desired.

One of the major factors of the tissue culture environment is light. The degree of organogenesis and plantlet formation is very much dependent upon intensity, length of the daily exposure period, and quality of illumination. However, information concerning the effects of spectral quality, or regions of light quality, on organogenesis is lacking.

SUMMARY OF THE INVENTION

A method for stimulating organogenesis of explants in a tissue culture is provided comprising the step of illuminating the explant during at least a portion of its differentiation stage with light having a predominate spectral emission at a wavelength of approximately 660nm. Further details concerning the disclosed method are discussed in the following description of the preferred embodiment including examples wherein the method is utilized for the organogenesis of lettuce and Douglas fir explants. The description of the preferred embodiment is to be read in conjunction with the following drawings which form a part thereof.

DESCRIPTION OF THE PREFERRED EMBODIMENT

The disclosed method for stimulating organogenesis of explants in a tissue culture medium may generally be utilized in conjunction with any of the tissue culture techniques known in the art. These techniques generally comprise the steps of excising an appropriate portion from a donor plant and placing the excised portion, or explant, on a culture medium. The method disclosed herein generally comprises the subsequent illumination of the explant with light having a predominant spectral emission at a wavelength of approximately 660nm once the explant has expanded and callus has formed thereon. As will be apparent from the following examples, it appears that the explants need not be illuminated during the induction phase of the tissue culture, but only during that portion of the differentiation stage in which the plants normally undergo bud formation. As is known in the art, the formation of these buds, which eventually transform into shoots and roots, occurs during approximately the second week of the culture. If the plants are illuminated in the manner hereindescribed subsequent to the bud formation period, the plants may appear greener and healthier owing to an increased presence of chlorophyll, but few additional shoots or roots are formed.

Figure 1:
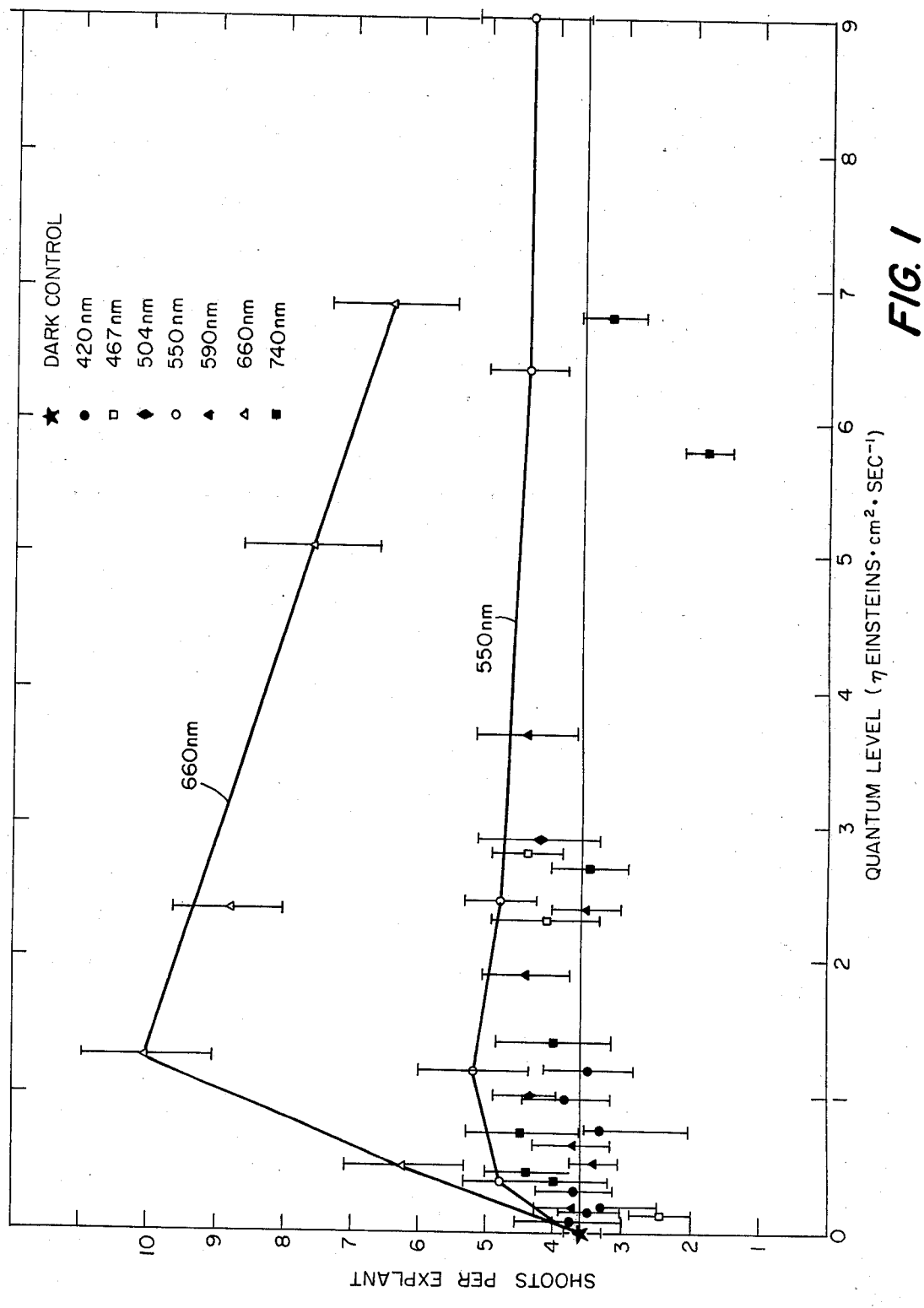
FIG. 1 is a graphic illustration showing the effect of various narrow-band light sources on lettuce explant organogenesis.

It is theorized that the phytochrome photoreceptor system of the plant is stimulated during the bud formation period by the 660nm light. The theory is supported by the finding that illumination of the explants with far-red light of approximately 740nm following illumination with 660nm light reverses and substantially neutralizes the effects thereof.

the following predominate spectral emissions: 371nm, 420nm, 467nm, 504nm, 590nm, 660nm, and 740nm, with intensities of 0.01mW/cm$^2$ to 2W/cm$^2$ for 16 hours per day. After 32 days, the total number of shoots and roots initiated were recorded. As shown in FIG. 1, the 660nm light caused a substantial increase in the number of shoots initiated per explant in comparison with control explants.

The effects of red light and far-red reversibility of red light were examined to determine whether the plant phytochrome system is responsible for the substantial increase in organogenesis. Two sets of experiments were designed. In the first, the plants were irradiated with red and/or far-red light applied immediately after their implantation in the tissue culture. The results, illustrated in Table 1 below, show a significant difference in the number of shoots formed 35 days after exposure, thereby indicating that the explants may be sensitive to initial light treatments.

TABLE 1

EFFECT OF BRIEF IRRADATION OF RED AND FAR-RED LIGHT ON THE CALLUS GROWTH AND SHOOT FORMATION IN LETTUCE COTYLEDON EXPLANTS

| TREATMENTS | MEANS TOTAL WEIGHT (g)/EXPLANT | NO. OF SHOOTS/ EXPLANT | CALLUS WEIGHT (g)/EXPLANT |
|---|---|---|---|
| Dark Control | 4.17 ± 0.35 (40) | 4.52 ± 0.23 | 2.33 ± 0.24 |
| 5 Min R − D | 3.53 ± 0.38 (30) | 5.57 ± 0.39* | 2.19 ± 0.25 |
| 5 Min R + 5 Min FR − D | 4.24 ± 0.35 (30) | 6.1 ± 0.37*** | 2.49 ± 0.24 |
| 5 Min FR − D | 4.33 ± 0.37 (30) | 5.46 ± 0.38* | 2.52 ± 0.27 |
| 150 Min R − D | 4.55 ± 0.38 (30) | 6.21 ± 0.41*** | 2.74 ± 0.25 |
| 150 Min R + 150 Min FR − D | 4.06 ± 0.38 (30) | 5.56 ± 0.46* | 2.46 ± 0.20 |
| 150 Min FR − D | 4.37 ± 0.31 (29) | 5.86 ± 0.42** | 2.52 ± 0.24 |

R: 660nm (240μW/cm$^2$); FR: 740 nm (680μW/cm$^2$); ±: 1 SEM
*0.05 ≥ p > 0.01 (t-Test in comparison with control value)
**0.01 ≥ p > 0.001 (t-Test in comparison with control value)
***0.001 ≥ p (t-Test in comparison with control value)

EXAMPLE I LETTUCE ORGANOGENESIS

Lettuce was selected as representative of the family Cruciferae because of the ease with which it may be grown.

Cotyledon explants measuring 3 × 2mm were obtained from 5 day old germinated seeds of Lactuca sativa var. 'Black Seeded Simpson'. The explants were cultured on a medium having the following composition:

| ORGANIC SALTS | (mg/l) | INORGANIC SALTS | (mg/l) |
|---|---|---|---|
| Thiamine . HCl | 0.1 | KH$_2$PO$_4$ | 300 |
| Nicotinic acid | 0.5 | KNO$_3$ | 1000 |
| Pyridoxine . HCl | 0.1 | NH$_4$NO$_3$ | 1000 |
| Myo-inositol | 100 | Ca(NO$_3$)$_2$ . 4H$_2$O | 500 |
| Glycine | 2 | MgSO$_4$ . 7H$_2$O | 71.6 |
| Sucrose | 30,000 | KCl | 65 |
| Agar | 10,000 | MnSO$_4$ . H$_2$O | 4.92 |
|  |  | ZnSO$_4$ . 7H$_2$O | 2.67 |
|  |  | H$_3$BO$_3$ | 1.6 |
|  |  | KI | 0.8 |
|  |  | NaEDTA | 37.2 |
|  |  | FeSO$_4$ . 7H$_2$O | 27.8 |
| GROWTH REGULATORS | (mg/l) |  |  |
| Indoleacetic Acid (IAA) | 1 |  |  |
| Kinetin | 0.5 |  |  |
| Adenine sulfate | 40 |  |  |

However, it may be noted from Table 1, that the far-red light at 740nm failed to bring about photoreversibility of the red light (660nm), strongly suggesting that the phytochrome is not involved in the regulation of shoot formation during its early phase of morphogenesis.

The second experiment, the results of which are shown in Table 2 below, demonstrates the stimulative effects of red light on shoot formation when daily illu- The cultures were then divided into a plurality of samples which were illuminated by light having one of mination is provided for a period of 35 days.

TABLE 2
FAR-RED REVERSIBILITY OF RED LIGHT INDUCED SHOOT FORMATION IN LETTUCE COTYLEDON EXPLANTS

| TREATMENTS | TOTAL WEIGHT (g) EXPLANT | NO. OF SHOOTS/ EXPLANT | CALLUS WEIGHT (g)/EXPLANT |
|---|---|---|---|
| Dark Control | 4.01 ± 0.35 (55) | 6.34 ± 0.56 | 2.25 ± 0.21 |
| 5 Min. R/Day | 6.75 ± 0.30 (30)*** | 16.96 ± 0.78*** | 3.25 ± 0.22** |
| 5 Min. R + 5 Min. FR/Day | 2.84 ± 0.47 (27) | 6.48 ± 0.92 | 1.70 ± 0.32 |

R: 660nm (240µW/cm$^2$); FR: 740nm (680µW/cm$^2$); ± 1 SEM
**0.01 ≥ p > 0.001 (t-Test in comparison with control value)
***0.001 ≥ p (t-Test in comparison with control value)

As shown in Table 2, five minutes of 660nm light per day at 240µW/cm$^2$ stimulates shoot formation by an amount comparable to that attained by illuminating the explants 16 hours/day at this wavelength and intensity. It may also be appreciated that the effects of red light on shoot formation were substantially neutralized by immediately following 5 minutes of red light exposure with 5 minutes of far-red light at 740nm and 680µW/cm$^2$: a comparison of the net response following the irradiation sequence of red plus far-red with the organogenesis of the dark control, provides proof that phytochrome is the photoreceptor involved in the stimulation of the shoot formation.

The data in Table 2 may be additionally interpreted as an indication that phytochrome-regulated shoot formation is a photomodulated, rather than photodetermined control mechanism. In photomodulation, the manifestation of photoresponses (increase of callus growth and shoot formation) intimately depends upon the continuous presence of the $P_{fr}$ photoreceptor in the plant biosystem as would be maintained by daily 5 minute exposures of red light. In photodetermination, the response, once triggered by a sufficient $P_{fr}$ level, would continue in the absence of further illumination.

Further experiments were conducted to determine the time during the five week culture period in which the 660nm light is most effective in promoting organogenesis. Groups of lettuce cotyledon explants were exposed daily to five minutes of 660nm light at 240µW/cm$^2$ during a different one of the five weeks, and the entire five week culture period. Comparison of these treatments from the data in Table 3 below shows that the cultures irradiated with 660nm light during the second week of the culture period produced more shoots than control cultures or cultures exposed to light during any other week of the culture period.

It may be appreciated that there was no significant difference in the number of shoots obtained in cultures exposed to light during only the second week or during all five weeks. These findings indicate that the phytochrome-mediated bud formation and shoot formation is most active during the second week of culture growth and that continual exposure with 660nm light is not required to increase organogenesis.

TABLE 3
ORGANOGENESIS RESPONSES OF LETTUCE COTYLDON TISSUE CULTURES TO 660nm LIGHT EXPOSURE GIVEN FOR SPECIFIC INTERVALS DURING THE CULTURE PERIOD

| ILLUMINATION INTERVAL | AVG. NO. OF SHOOTS/EXPLANT |
|---|---|
| Control | 4 |
| week 1 | 4.25 |
| week 2 | 7 |
| week 3 | 5.1 |
| week 4 | 4.6 |
| week 5 | 4.6 |
| 5 weeks | 6.5 |

Experiments were next conducted to determine if the 660nm light enhanced shoot formation in lettuce cotyledon explants by stimulating bud formation or by increasing bud development. Lettuce cotyledon explants were exposed to 5 minutes of 660nm light at 240µW/cm$^2$ per day. To distinguish between shoot formation increases due to the increased differentiation of existing buds into shoots, and increased shoot formation due to enhanced shoot initiation through the stimulation of bud formation, the number of organs initiated at an early stage of culture development were then examined. In Table 4 below, the number of buds, shoots and roots formed after 14 days in treated cultures, were compared with those formed in the control cultures.

TABLE 4
ORGAN FORMATION IN LETTUCE COTYLEDON AFTER 14 DAYS IN CULTURE

| TREATMENT | BUDS | SHOOTS | ROOTS | TOTAL ORGANS | SHOOTS TOTAL ORGANS |
|---|---|---|---|---|---|
| A. 5 Min/Day 660nm (240µW/cm$^2$) | 30.34 ± 0.74 (26)+++ | 3.00 ± 0.34+ | 1.33 ± 0.27++ | 24.67 ± 0.86 | 0.123 |
| B. Control | 11.23 ± 1.14 (30) | 1.47 ± 0.22 | 0.23 ± 0.1 | 12.93 ± 1.18 | 0.114 |
| C. B/A | 0.55 | 0.49 | 0.17 | 0.52 | 0.93 |

+0.05 ≥ p > 0.01 Smirnov test in comparison with control
++0.01 ≥ p > 0.001 Smirnov test in comparison with control
+++0.001 ≥ p Smirnov test in comparison with control As shown in Table 4, illuminated samples formed more buds, as well as shoots, than did control cultures. Since shoots develop from buds, it appears that the increased number of shoots formed in the cultures after either 14 or 35 days is due to an increase in the number of buds formed. This observation is strengthened by the fact that after 14 days the ratio of shoots to total organs in the lighted samples (0.123) was very close to that of the controls (0.114). It may, thus, be concluded that 660nm light stimulates the shoot formation process by increasing the formation of buds in a phytochromerelated process. Once the buds are initiated, a certain percentage will differentiate into shoots independent of red light exposure.

EXAMPLE 2 DOUGLAS FIR

Douglas fir embryos were derived from seeds which had been decoated and sterilized with a 25% solution of Chlorox bleach for 20 minutes. The embryo was placed on a culture medium comprising:

| INORGANIC SALTS | (mg/l) |
|---|---|
| $NH_4NO_3$ | 1650 |
| $KNO_3$ | 1900 |
| $CaCl_2 . 2 H_2O$ | 440 |
| $MgSO_4 . 7H_2O$ | 370 |
| $KH_2PO_4$ | 170 |
| $FeSO_4 . 7H_2O$ | 27.8 |
| NaEDTA | 37.2 |
| $MnSO_4 . 4 H_2O$ | 22.3 |
| $ZnSO_4 . 7H_2O$ | 10.51 |
| KI | 0.83 |
| $NaMoO_4 . 2H_2O$ | 0.25 |
| $CuSO_4 . 5H_2O$ | 0.025 |
| $CoCl_2 . 6H_2O$ | 0.025 |
| $H_3BO_3$ | 1.6 |
| ORGANIC SALTS | (mg/l) |
| Thiamine . HCl | 5 |
| Nicotinic Acid | 0.1 |
| Pyridoxine . HCl | 0.1 |
| Myo-inositol | 500 |
| Sucrose | 30,000 |
| Agar | 8,000 |
| GROWTH REGULATORS | |
| Indoleacetic acid | 0.8 mg/l |
| Indole-3-beutyric acid | 1 mg/l |
| $N_6$-Benzyladenine | 1 mg/l |
| $\Delta^5$-isopentyl-adenine | 1 mg/l |

Following callus induction, Douglas Fir embryo explants undergo a bud primordia formation stage for 7 to 10 days during which a second medium comprising the foregoing components supplemented by 1mM of $N_6$-Benzyladenine and 0.5mM of Zeatin. Finally, the bud primordia is allowed to undergo adventitious bud formation stage 18 to 24 days in a culture medium comprising half the concentration of the inorganic and organic salts associated with its first stage medium but which contains no hormones or hormonal supplements.

The cultures have been illuminated according to the disclosed method during all three of the stages, although illumination is not required during the first stage.

embryo explants in a tissue culture. It may be appreciated that the light wavelengths of 550nm, 590nm, and 660nm caused a significant increase in the number of adventitious buds formed per explants in comparison with the dark controls.

Predominant root formation has been found to occur under 740nm (0.22 to 0.9$\mu$W/cm$^2$) light. It is accordingly preferable to subject the cultures to 660nm light to trigger the formation of adventitious buds and to subsequently subject the cultures to 740nm light to stimulate maximum root formation. As is known in the art, however, the effects of 660nm and 740nm light have mutually reversible effects on phytochrome-controlled processes such as organogenesis. It is, therefore, necessary to include an intervening period, preferably one or two weeks between the 660nm and 740nm light treatments.

It is also preferable for the sake of convenience to stimulate shoot formation prior to root formation. A culture medium which is conductive to shoot formation contains a root-inhibiting concentration of Kinetin which is depleted during the shoot-initiating illumination of the culture with 660nm light. Accordingly, the medium will accommodate root formation during the subsequent 740nm illumination.

It has additionally been found, as shown in Tables 5 and 6 below, that the orientation of the embryonic axis within the culture medium and the culturing of specific embryonic portions unexpectedly effect the rate of organogenesis.

In order to determine the influence of embryonic axis orientation and regions on organogenesis, two sets of experiments were designed. In one set, an intact embryo was planted either with its proximal (radicle end) or distal (needle or cotyledon end) portion in medium. In the second set, an intact embryo was divided into three equal parts and each of them planted separately onto the medium.

Table 5 shows the effect of embryonic axis orientation on organogenesis. Over 90% embryos produced adventitious buds when they were planted with their distal region in contact with the medium. The adventitious buds developed sooner and generally were greater in number than those obtained with intact embryos having their proximal ends in medium.

TABLE 5

EFFECT OF EMBRYONIC AXIS ORIENTATION ON ORGANOGENESIS IN DOUGLAR FIR TISSUE CULTURES

| Axis Orientation | Percentage of Embryos Differentiated | Time to Differentiation (Days) | Callus Wt/ Embryo | No. of Adventitious buds/ Embryo | No. of shoots/ Embryo |
|---|---|---|---|---|---|
| Proximal End in Medium | 30 | 40 | 0.546 ± 0.062 (40) | 3.8 ± 1.2 | 3 ± 0.85 |
| Distal End in Medium | 94 | 25 | 0.858 ± 0.042 (38) | 12.4 ± 1.6 | 9.4 ± 1.1 |

Figure 2:
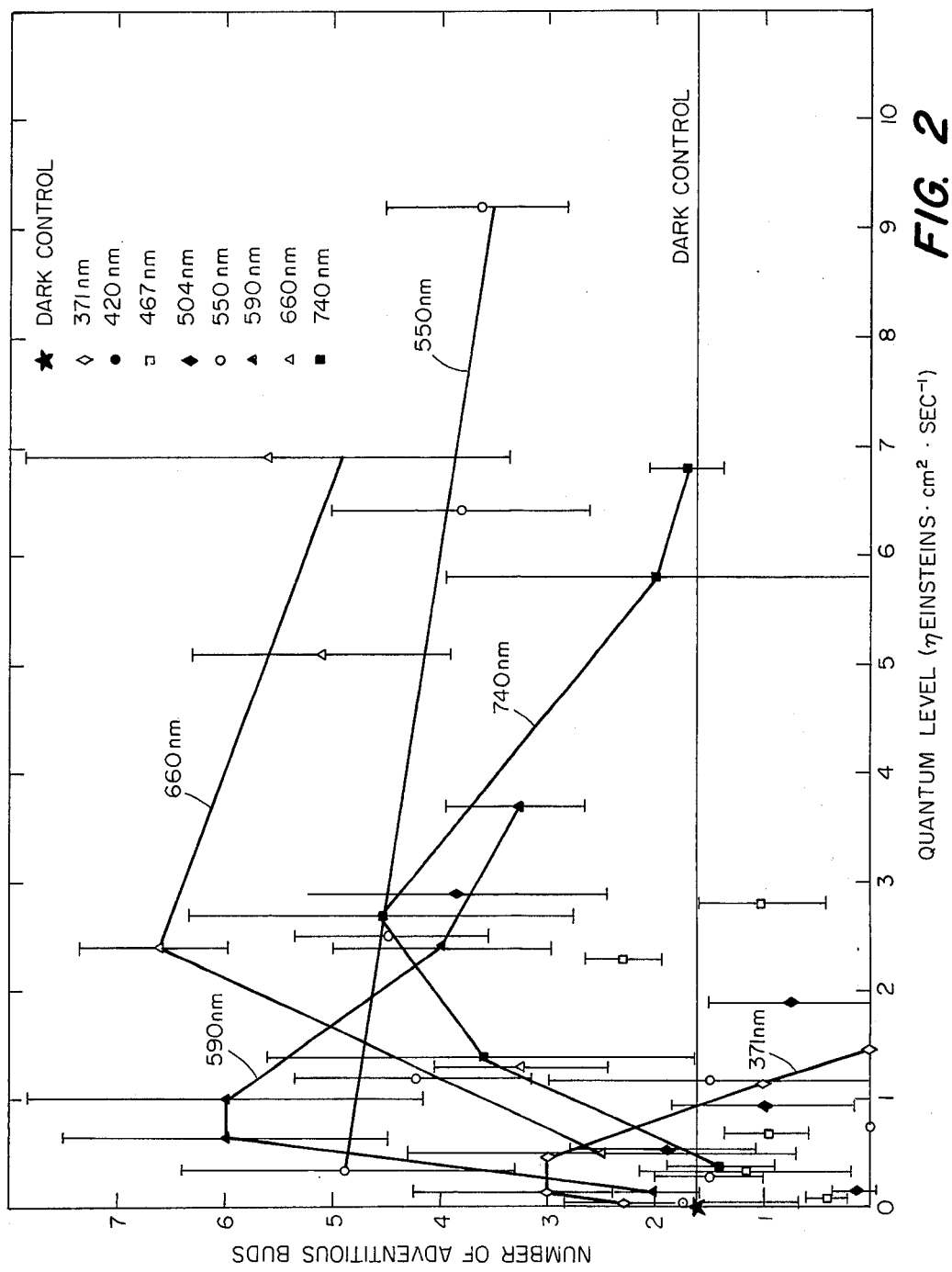
FIG. 2 is a graphic illustration showing the effect of various narrow-band light sources on Douglas fir embryo organogenesis.

FIG. 2 graphically illustrates the influence of light quality on the organ forming capacity of Douglas Fir

TABLE 6

INFLUENCE OF EMBRYONIC REGIONS ON ORGANOGENESIS IN DOUGLAR FIR TISSUE CULTURES

| Embryo region | Time to Differentiation (Days) | Callus Wt/ Explant | No. of Adventitious buds/ explant | No. of Shoots/ explant |
|---|---|---|---|---|
| Proximal | 45 | 0.496 ± 0.092 (30) | 3.5 ± 0.65 | 2.3 ± 0.59 |
| Middle | — | 0.570 ± 0.051 (30) | — | — |
| Distal | 25 | 0.791 ± 0.038 (30) | 9.7 ± 1.1 | 6.8 ± 0.72 |

As shown in Table 6, a significant increase in both callus weight (t-test, $0.05 \geq p$) and the number of adventitious buds and shoots was observed among the cultured distal portions, as compared to the other parts of embryo. The procedures developed here for initiating buds and shoots from Douglas fir embryos were next tested to determine the extent of their application. The results indicate that the same technique is applicable to the other trees including embryos of western hemlock, balsam fir and pine trees.

While the foregoing description and examples illustrate the preferred method for promoting organogenesis of selected explants in a tissue culture, it is intended that the invention be defined only by the following appended claims.

I claim:

1. A method for stimulating organogenesis of explants in a tissue culture medium comprising the step of:
    illuminating the explant during at least a portion of its differentiation stage with light having a predominate spectral emission at approximately 660nm.

2. The method of claim 1 wherein the donor plant is selected from the group consisting of lettuce, fir trees and pine trees.

3. The method of claim 1 wherein the explants are illuminated for a period of approximately 5 minutes per day.

4. The method of claim 1 wherein the light intensity is in the range of approximately 0.010 to 2.0 mW/cm$^2$.

5. The method of claim 1 wherein the explants are only illuminated during approximately the second week of the culture period.

6. A method for stimulating organogenesis of explants in a tissue culture medium comprising the steps of:
    placing an embryo of the donor plant in a culture medium;
    illuminating the cultured embryo with light having a predominate spectral emission at a wavelength of approximately 660nm to induce shoot formation; and
    illuminating the cultured embryo with light having a predominate spectral emission at a wavelength of approximately 740nm to stimulate root formation, an intervening period being provided between the two illuminations sufficiently long to prevent photoreversibility of the firstly stimulated effect.

7. The method of claim 6 wherein the cultured embryo is initially illuminated with the 660nm light.

8. The method of claim 6 wherein the intervening period is from one to two weeks.

9. A method for stimulating organogenesis of embryo explants in a tissue culture medium comprising the steps of:
    placing only the distal or cotyledon end of the embryo in the culture medium and
    illuminating the embryo during at least a portion of its differentiation stage with light having a predominate spectral emission of approximately 660nm.

10. The method of claim 9 including the step of:
    illuminating the cultured embryo with light having at predominate spectral wavelength of 740nm, an intervening period being established between the two illumination periods to generally prevent photoreversibility of the firstly stimulated organ forming process.

11. The method of claim 9 wherein the distal or cotyledon end has been excised from the embryo prior to placement in the culture medium.

* * * * *

UNITED STATES PATENT OFFICE
CERTIFICATE OF CORRECTION

Patent No. 4,060,933          Dated December 6, 1977

Inventor(s)  PRAKASH G. KADKADE

It is certified that error appears in the above-identified patent and that said Letters Patent are hereby corrected as shown below:

Column 3, Table 1, line 8, delete "5 Min R - D" and
insert --5 Min R→D--;

line 10, delete "FR - D" and
insert --FR→D--;

line 11, delete "5 Min FR - D" and
insert --5 Min FR→D--;

line 12, delete "150 Min R - D"; and
insert --150 Min R→D--;

line 14, delete "Min FR  D" and
insert --Min FR→D--;

line 15, delete "150 Min FR  D" and
insert --150 Min FR→D--.

Signed and Sealed this

Eighteenth Day of April 1978

[SEAL]

Attest:

RUTH C. MASON
Attesting Officer

LUTRELLE F. PARKER
Acting Commissioner of Patents and Trademarks